US007807476B2

(12) United States Patent
Pressman et al.

(10) Patent No.: US 7,807,476 B2
(45) Date of Patent: Oct. 5, 2010

(54) VIAL SYSTEM AND METHOD FOR PROCESSING LIQUID-BASED SPECIMENS

(75) Inventors: Norman J. Pressman, Glencoe, IL (US); William J. Mayer, South Barrington, IL (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 12/732,078

(22) Filed: Mar. 25, 2010

(65) Prior Publication Data

US 2010/0178711 A1 Jul. 15, 2010

Related U.S. Application Data

(62) Division of application No. 10/122,151, filed on Apr. 15, 2002.

(60) Provisional application No. 60/330,092, filed on Oct. 19, 2001.

(51) Int. Cl.
G01N 1/18 (2006.01)

(52) U.S. Cl. .................. 436/177; 436/174; 436/178; 422/100; 422/101; 422/102

(58) Field of Classification Search .............. 422/99, 422/100, 101, 102; 435/283.1, 288.1; 436/63, 436/64, 174, 177, 178
See application file for complete search history.

(56) References Cited

U.S. PATENT DOCUMENTS

| 2,143,044 A | 1/1939 | Wicks et al. |
| 4,078,692 A | 3/1978 | Stein |
| 4,184,483 A | 1/1980 | Greenspan |
| 4,735,905 A | 4/1988 | Parker |
| 4,842,826 A | 6/1989 | Guala |
| 5,143,627 A | 9/1992 | Lapidus et al. |
| 5,301,685 A | 4/1994 | Guirguis |
| 5,422,273 A | 6/1995 | Garrison et al. |
| 5,429,803 A | 7/1995 | Guirguis |
| 5,431,884 A | 7/1995 | McDonough et al. |

(Continued)

FOREIGN PATENT DOCUMENTS

EP 1014088 A2 6/2000

(Continued)

OTHER PUBLICATIONS

Office Action mailed on Oct. 28, 2008 in U.S. Appl. No. 12/007,158. Inventor Norman Pressman, (11 pages).

(Continued)

*Primary Examiner*—Jill Warden
*Assistant Examiner*—Dwayne K Handy
(74) *Attorney, Agent, or Firm*—Vista IP Law Group LLP

(57) ABSTRACT

A vial-based system and method for handling and processing specimens of particulate matter-containing liquid directly in the vial. A processing assembly, which includes a stirrer and a particulate matter separation chamber, is releasably coupled to the inside of the vial cover. The processing assembly remains with the cover when the vial is opened to insert a specimen therein. Application of a particular external force to the closed vial detaches the processing assembly from the cover so that it remains in the vial, for access by automated or manual laboratory equipment, when the cover is subsequently removed.

24 Claims, 12 Drawing Sheets

U.S. PATENT DOCUMENTS

Figure 1:
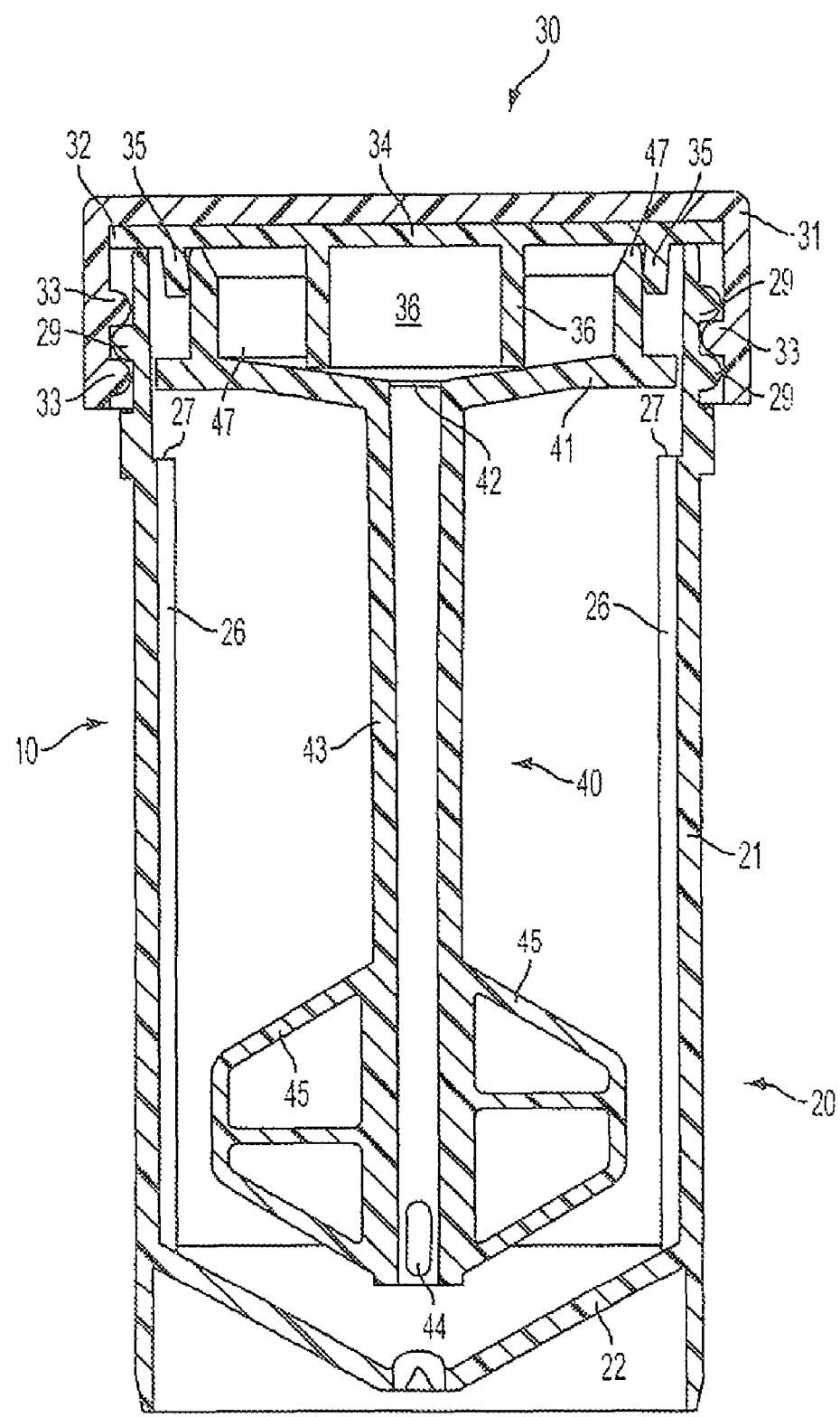

| | | |
|---|---|---|
| 5,471,994 A | 12/1995 | Guirguis |
| 5,500,184 A | 3/1996 | Palmer |
| 5,624,554 A | 4/1997 | Faulkner et al. |
| 5,833,928 A | 11/1998 | Ratajczak et al. |
| 6,296,764 B1 | 10/2001 | Guirguis et al. |
| 6,302,268 B1 | 10/2001 | Michaeli |
| 6,309,362 B1 | 10/2001 | Guirguis |
| 6,358,474 B1 | 3/2002 | Dobler et al. |
| 6,423,237 B1 | 7/2002 | Guirguis |
| 6,440,373 B1 | 8/2002 | Gomes et al. |
| 6,830,935 B1 | 12/2004 | El-Amin et al. |
| 6,846,028 B2 | 1/2005 | Pratt |
| 7,147,826 B2 | 12/2006 | Haywood et al. |
| 2003/0069413 A1 | 4/2003 | Pai et al. |

FOREIGN PATENT DOCUMENTS

| | | |
|---|---|---|
| WO | WO 9902958 A1 | 1/1999 |
| WO | WO 9923468 A1 | 5/1999 |

OTHER PUBLICATIONS

International Search Report and Written Opinion for related application PCT/US02/33459, dated Jun. 2, 2003, Forms PCT/ISA/220 and 210, Applicant Monogen, Inc., (6 pages).

Written Opinion for related application PCT/US02/33459, dated Sep. 7, 2003, Forms PCT/IPEA/408 and form PCT/408AE1, Applicant Monogen, Inc. et al. (2 pages).

International Preliminary Examination Report for related application PCT/US02/33459, dated Dec. 17, 2003, Applicant Monogen, Inc. et al. (9 pages).

VIAL SYSTEM AND METHOD FOR PROCESSING LIQUID-BASED SPECIMENS

RELATED APPLICATION DATA

This application is a divisional of U.S. patent application Ser. No. 10/122,151, filed Apr. 15, 2002, which claims the benefit of U.S. provisional application No. 60/330,092, filed Oct. 19, 2001, which is incorporated herein by reference. Application Ser. No. 10/122,151 is also related to commonly owned U.S. provisional application No. 60/372,080, filed Apr. 15, 2002, which is also incorporated herein by reference.

BACKGROUND

The present invention is directed to an apparatus and a method for collecting and processing specimens of biological fluid, including collecting uniform layers of cells therefrom suitable for use in cytology protocols.

In a wide variety of technologies, the ability and/or facility in separating matter, typically particulate matter, from a fluid is a critical component in the ability to test for the presence of substances in the fluid. Too often, interference associated with sample preparation obscures the target particles to such a degree that the process is not sufficiently reliable, or too costly. Such problems exist in various fields of examination which involve detection and/or diagnosis, including environmental testing, radiation research, cancer screening through cytological examination, microbiological testing, and hazardous waste contamination, to name just a few.

Cytological examination of a sample begins with obtaining specimens including a sample of cells from the patient, which can typically be done by scraping or swabbing an area, as in the case of cervical samples, or by collecting body fluids, such as those obtained from the chest cavity, bladder, or spinal column, or by fine needle aspiration or fine needle biopsy. In a conventional manual cytological preparation, the cells in the fluid are then transferred directly onto a glass slide for viewing. In a conventional automated cytological preparation, a filter assembly is placed in the liquid suspension and the filter assembly both disperses the cells and captures the cells on the filter. The filter is then removed and placed in contact with a microscope slide.

In all of these endeavors, a limiting factor in the sample preparation protocol is adequately separating solid matter from its fluid carrier, and in easily and efficiently collecting and concentrating the solid matter in a form readily accessible to microscopic examination. Diagnostic microbiology and/or cytology, particularly in the area of clinical pathology, bases diagnoses on a microscopic examination of cells and other microscopic analyses. The accuracy of the diagnosis and the preparation of optimally interpretable specimens typically depends upon adequate sample preparation. In this regard the ideal specimen would consist of a monolayer of substantially evenly spaced cells. Newer methodologies such as immunocytochemistry and image analysis require preparations that are reproducible, fast, biohazard-free and inexpensive.

Currently, biological samples are collected for cytological examinations using special containers. These containers usually contain a preservative solution for preserving the cytology specimen during shipment from the collection site to the cytology laboratory. Further, cytology specimens collected from the body cavities using a swab, smear, spatula or brush are also preserved in special containers with fixatives (e.g., alcohol or acetone fixatives) prior to transferring cells onto the slide or membrane for staining or examination.

Specimen containers are known that allow a liquid-based biological specimen to be processed directly in the container so as to obtain a substantially uniform layer of cells on a collection site (in a filter housing defining a particulate matter separation chamber) that is associated with the container itself. See, for example, U.S. Pat. Nos. 5,301,685; 5,471,994; 6,296,764; and 6,309,362, all of which are incorporated herein by reference. However, these types of specimen containers require specially configured apertured covers and adapters therefor that are designed to mate with the filter housing, and with suction equipment (e.g., a syringe or a mechanized vacuum source) used to aspirate liquid from the container and draw it through the filter. Further, extraction of the filter so that it can be pressed against a microscope slide to transfer collected cells to the slide requires disassembly of the cooperating parts of the cover and/or adapters associated therewith. If the processing is done by automated equipment, special handling devices are required to carry out such disassembly. All of this complexity adds time and material and labor cost to the processing required prior to the actual cytology examination.

SUMMARY OF THE INVENTION

The present invention concerns a specimen vial that houses a complete processing assembly, typically one for stirring the liquid-based specimen therein and for holding a filter on which a uniform layer of cells can be collected from the specimen. It is expected that the specimen vial would be prepackaged with a liquid preservative solution, as is commonplace.

The processing assembly is coupled to a simple cover for the vial by means of a simple and inexpensive releasable coupling. When the cover is removed at the point-of-care site (doctor's office, clinic, hospital, etc.), the processing assembly remains with the cover to allow medical personnel easy access to the container interior for insertion of a biological specimen into the vial. The cover, along with the attached processing assembly, is then replaced to seal the vial. The vial may then be sent to a laboratory for processing.

When the vial is manipulated in a simple way while still closed, the processing assembly detaches from the cover and remains in the vial for access by automated or manual laboratory equipment when the cover is subsequently removed. In a preferred embodiment, a downward force on the center of the cover is all that is required to detach the processing assembly from the cover. In contrast with the prior art specimen vials discussed above, the vial of the present invention requires no further interaction with the cover, which can be removed by a simple uncapping device and is discarded to avoid contamination.

Accordingly, a first aspect of the invention concerns a method for processing particulate matter-containing liquid in a vial comprising a container having an opening at its upper end, a cover removably coupled to the container to close the opening, and a processing assembly releasably coupled to the cover. The method comprises the steps of detaching the processing assembly from the cover while the cover is on the container, removing the cover to expose the detached processing assembly in the container, and manipulating the processing assembly so as to process the particulate matter-containing liquid in the container. The detaching step comprises applying an external force to the closed vial. The external force may be applied to the central portion of the cover to deflect the cover inwardly.

The processing assembly may comprise a dispersing element, and the manipulating step may comprise moving at least the dispersing element to disperse the particulate matter in the liquid. The dispersing element may be rotated to stir the liquid. Before such rotation, the dispersing element may first be lifted slightly to insure clearance between the processing assembly and the container.

The processing assembly may comprise a particulate matter separation chamber at the upper portion thereof adapted to hold a filter assembly, and a tube communicating with the separation chamber and extending downwardly therefrom. With such an arrangement the manipulating step may comprise placing a filter assembly in the separation chamber, sealing the separation chamber, and applying a vacuum to the separation chamber to draw the stirred particulate matter-containing liquid upwardly through the tube and into contact with the filter assembly so as to collect particulate matter on a surface of the filter assembly. Then the filter assembly may be removed from the separation chamber, and the particulate matter collected on the filter assembly contacted with a slide so as to transfer collected particulate matter to the slide.

Another aspect of the invention concerns a vial for holding and processing particulate matter-containing liquid. The vial comprises a container having an opening at its upper end, a cover removably coupled to the container to close the opening, and a processing assembly releasably coupled to the cover so as to be removable from the container with the cover while still coupled thereto, and selectively detachable from the cover while the cover is on the container so as to remain in the container when the cover is subsequently removed.

The releasable coupling between the cover and the processing assembly may comprise mating couplers, respectively carried by the inside of the cover and the upper portion of the processing assembly, that are held together by a retention force and disengage upon application of an external force to the vial that overcomes the retention force. The couplers may mate and disengage by relative motion in the axial direction, i.e., parallel to the central axis of the container. The retention force may be frictional, and the couplers may be press-fit together.

The couplers may take the form of closely fitting projections, which may be annular. The upper portion of the processing assembly may comprise a bottom wall extending transversely of the container axis, the annular projection on the processing assembly extending upwardly from the bottom wall to form a cup-shaped recess (which may define a particulate matter separation chamber adapted to hold a filter assembly). The bottom wall may have a central hole, in which case a tube communicates with the hole and extends downwardly from the bottom wall. The tube has at least one dispersing element for dispersing particulate matter in the liquid.

The cover may have a central boss that extends into the cup-shaped recess when the processing assembly is coupled to the cover, the distal end of the central boss contacting or lying close to the bottom wall. When an external force is applied to the central portion of the cover so as to deflect the cover inwardly, the central boss presses against the bottom wall and pushes the bottom wall and the annular projection thereon away from the cover. The annular projection on the bottom wall may fit within the annular projection on the cover, so the external force deflects the annular projection on the cover outwardly, away from the annular projection on the bottom wall.

Yet another aspect of the invention concerns a vial for holding and processing particulate matter-containing liquid. The vial comprises a container having an opening at its upper end, a cover removably coupled to the container to close the opening, and a processing assembly wholly within the container and engageable by an external manipulator after the cover is removed. The container has a central axis extending lengthwise thereof through the opening, and a wall surrounding the axis. A portion of the surrounding container wall below the opening supports the processing assembly when it is not engaged by a manipulator such that the upper portion of the processing assembly is disposed near the opening.

The supporting portion of the container wall may comprise at least three spaced inwardly extending supports on which the processing assembly rests. These supports may comprise ribs (preferably four) that extend lengthwise of the container.

The processing assembly may comprise a particulate matter separation chamber at the upper portion thereof adapted to hold a filter assembly, a tube communicating with the separation chamber and extending downwardly therefrom, and a dispersing element carried by the tube. The upper portion of the processing assembly has a peripheral portion that lies close to the surrounding wall and rests on the ribs. The processing assembly may be rotated about the central axis so as to cause the dispersing element to stir the particulate matter-containing liquid, the processing assembly being dimensioned to rotate freely in the container without contacting the surrounding wall when lifted slightly off the ribs by a rotating manipulator. The close-fitting peripheral portion of the processing assembly prevents liquid from splashing out of the container during stirring, thus minimizing biohazard exposure. The ribs aid in the dispersion of particulate matter in the liquid.

BRIEF DESCRIPTION OF THE DRAWING FIGURES

A preferred embodiment that incorporates the best mode for carrying out the invention is described in detail below, purely by way of example, with reference to the accompanying drawing, in which:

FIG. 1 is a vertical sectional view through a specimen vial according to the invention, showing the processing assembly in the vial coupled to the cover;

FIG. 2*a* is a front elevational view of the container portion of the vial;

FIG. 2*b* is a top plan view of the container, shown with the processing assembly removed;

FIG. 3 is a top plan view of the processing assembly;

FIG. 4 is a bottom plan view of the liner that fits within the cover;

FIG. 5 is an exploded vertical sectional view of the processing assembly and a filter assembly adapted for use in the processing assembly;

FIG. 6 is a vertical sectional view of the upper portion of the processing assembly, showing the filter assembly in place in the particulate matter separation chamber and engaged by a suction head;

FIG. 7 is a partial schematic view of the arrangement depicted in FIG. 6, showing the flow of liquid and particulate matter separated therefrom;

FIG. 8 is a vertical sectional view of the specimen vial similar to FIG. 1, but showing the processing assembly detached from the cover;

FIGS. 9-13 are vertical sectional views of a container according to the invention undergoing various stages of automated laboratory handling, as follows:

FIG. 9 shows uncapping of the container (cover removal);

FIG. 10 shows primary stirring of the specimen;

FIG. 11 shows placement of a filter in the particulate matter separation chamber of the processing assembly;

FIG. 12 shows acquisition of a specimen on the filter by aspiration of liquid through the processing assembly;

Figure 13:
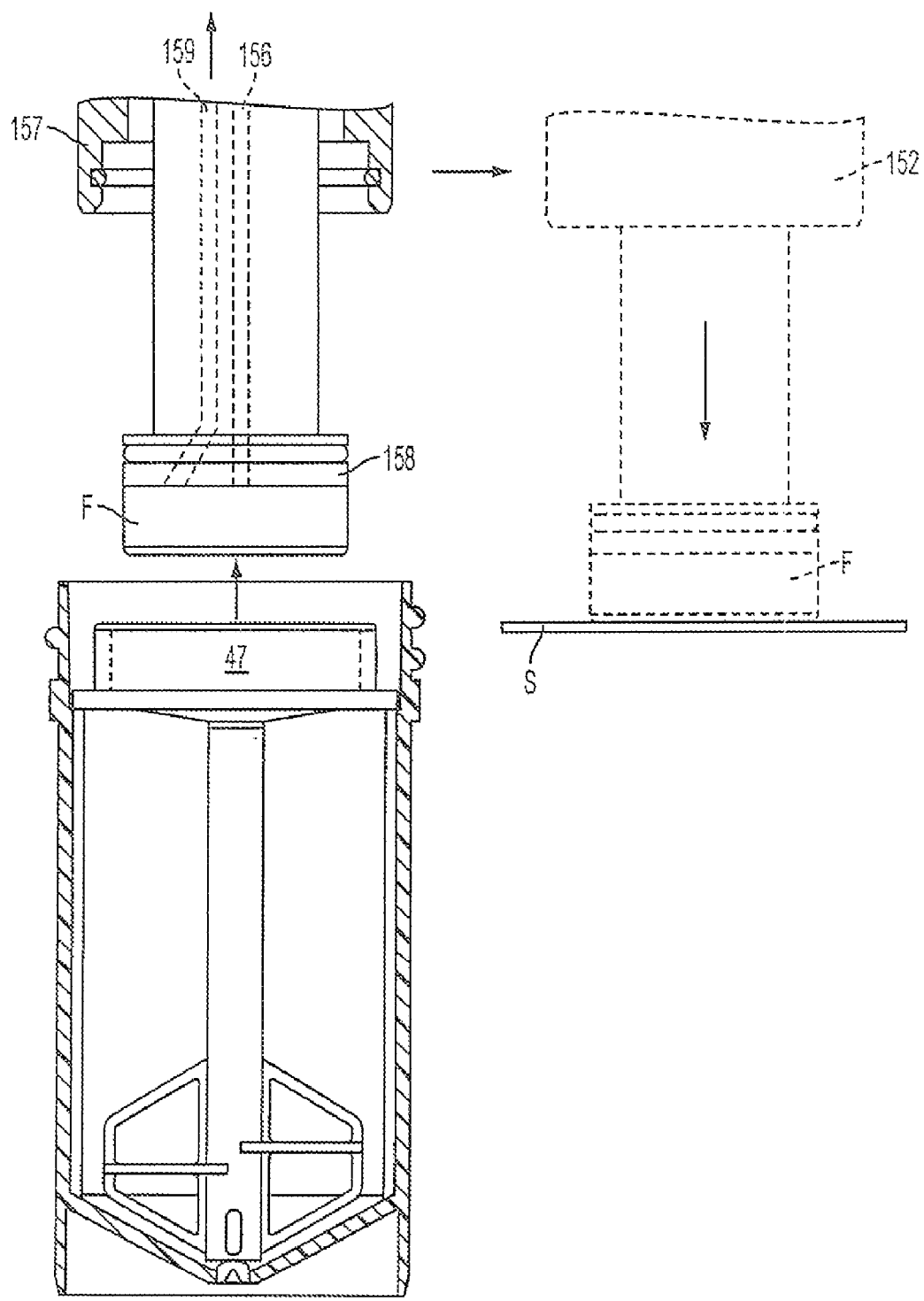
Figure 14:
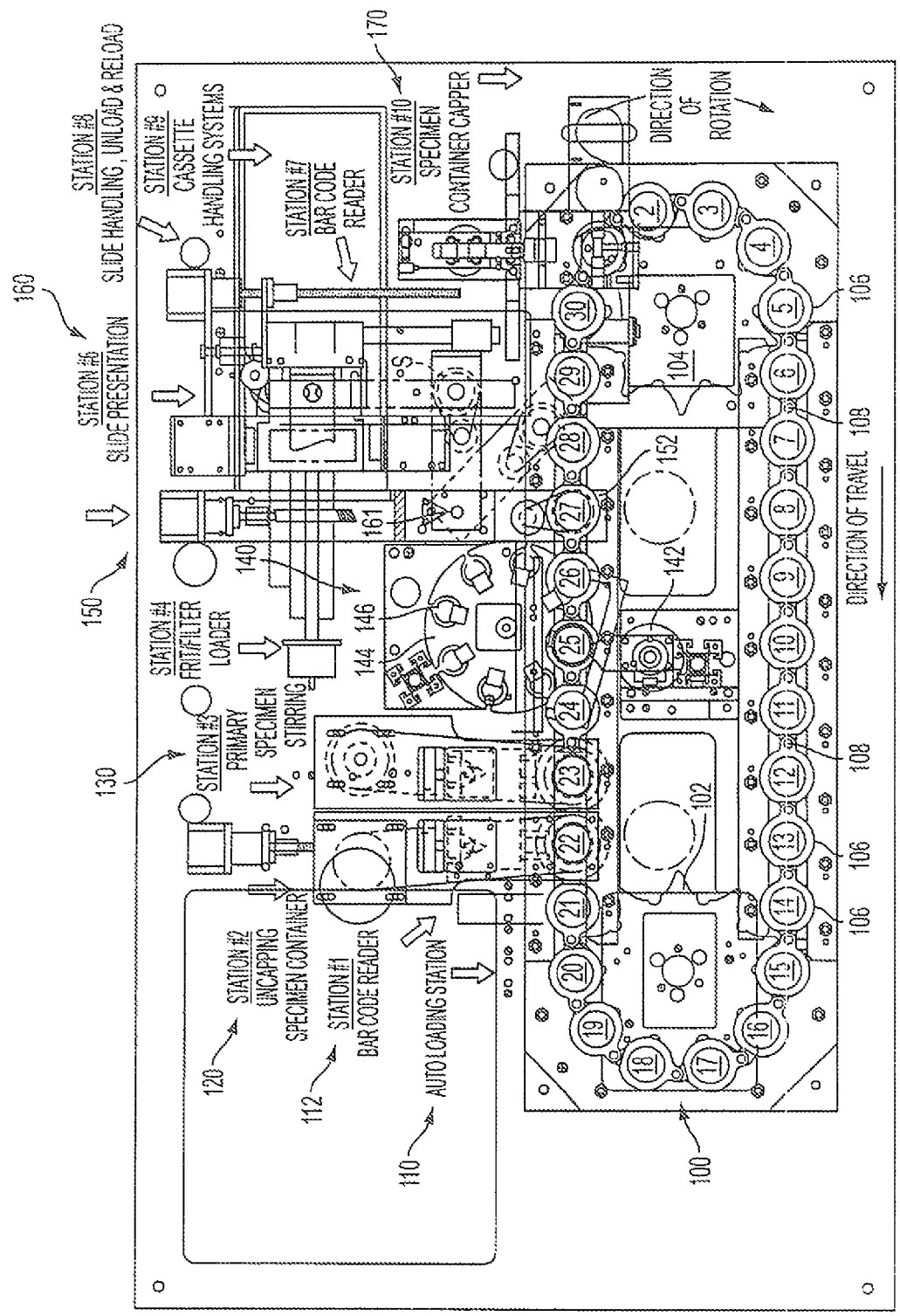

FIG. 13 shows removal of the filter and transfer of the specimen to a microscope slide; and FIG. 14 is a top plan view of an automated apparatus for handling vials according to the invention and carrying out the specimen processing steps illustrated in FIGS. 9-13.

It is to be understood that the invention is not limited in its application to the details of construction and the arrangement of components of the preferred embodiment described below and illustrated in the drawing figures. Further, while the preferred embodiment is disclosed as primarily useful in the collection and processing biological fluids for cytology examination, it will be appreciated that the invention has application in any field in which samples of particulate matter are to be prepared from a liquid that contains such particulate matter.

DETAILED DESCRIPTION

Figure 2A:
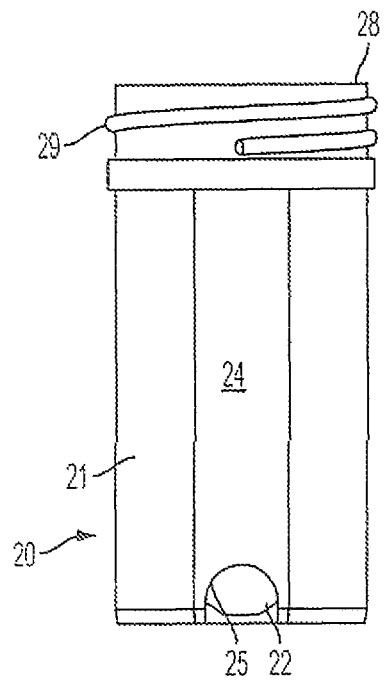
Figure 2B:
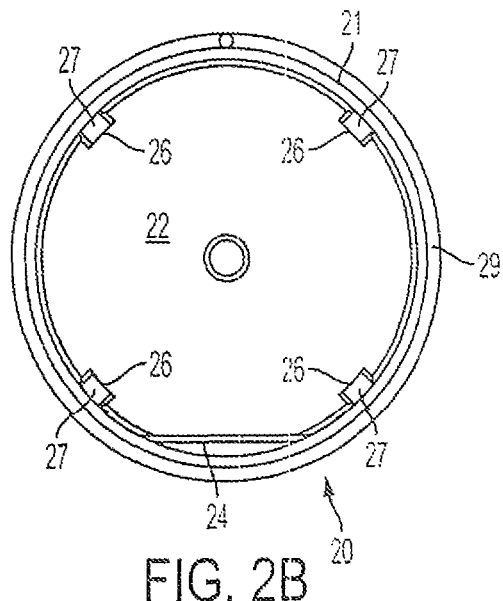
Figure 8:
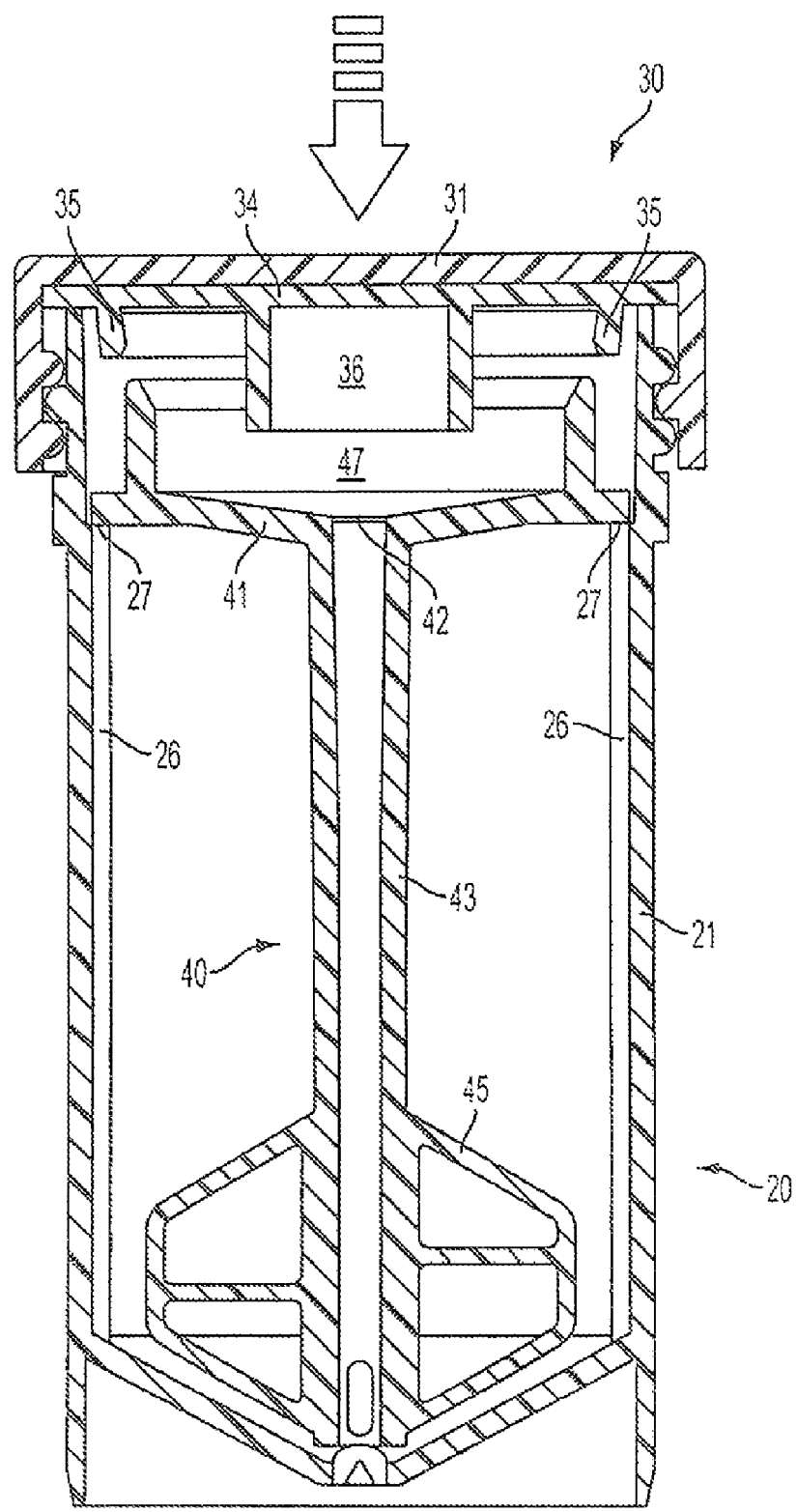

Referring to FIGS. 1, 2a and 2b, a vial 10 according to the invention comprises a container 20, a cover 30 and a processing assembly 40. Container 20 is molded of plastic, preferably polypropylene, and has a substantially cylindrical wall 21, surrounding its longitudinal axis, joined to a conical bottom wall 22. A small portion 24 of wall 21 is flat, the outer surface of the flat portion adapted to receive indicia, e.g., a bar code label, containing information concerning the specimen placed in the vial. Although only one flat portion is shown, the container could be configured with two or more flat portions, each adapted to receive indicia. The bottom end of flat portion 24 has an arcuate notch 25 which acts to keep the container in a proper orientation when handled by automated laboratory processing equipment designed to cradle the container and move it through various processing stations. Four longitudinal ribs 26 project inwardly from wall 21. The upper ends 27 of ribs 26 form rests for the processing assembly 40 when it is detached from cover 30 (see FIG. 8). The top of container 20 has an opening 28 and a standard right-hand helical thread 29 that preferably extends for one and one half turns and mates with a similar thread on cover 30. Other types of cover-to-container coupling may be used, such as a bayonet coupling, snap-fit arrangement, etc.

Figure 4:
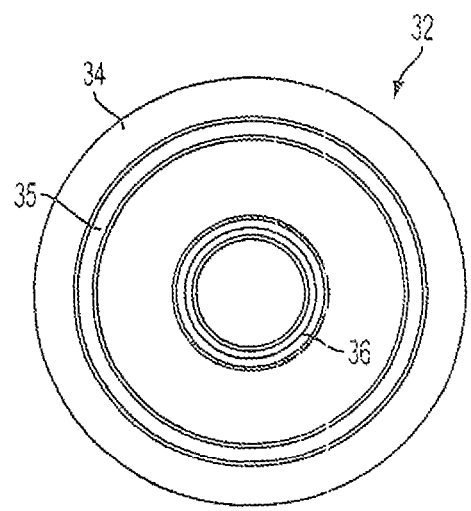

Cover 30 comprises a commercially available simple molded plastic threaded cap 31, and a novel liner 32 retained in the cap. Cap 31 has a flat solid top, and an externally knurled depending flange with an internal helical thread 33 that mates with thread 29 on container 20. Referring to FIG. 4, liner 32 is molded of plastic material, preferably polyethylene, and has a substantially flat base 34 sized to fit snugly within cap 31, behind thread 33, so that the liner is not readily separated from the cap. As seen in FIG. 1, liner base 34 serves as a seal between the cap 31 and the rim of the container wall 21.

Liner base 34 has a coupler in the form of an annular projection 35 that preferably is slightly conical in shape, preferably forming an angle of about 5.degree. to its central axis. In other words, the inner diameter of annular coupler 35 is greater at its proximal end, where it joins liner base 34, than at its distal end. Liner base 34 also has a central annular boss 36 that projects further from base 34 than annular coupler 35 so as to interact with processing assembly 40, as described below. While the use of a separate liner mated to a standard cap is preferred, the cover could be integrally molded in one piece to include the annular coupler 35 and the central annular boss 36.

Figure 3:
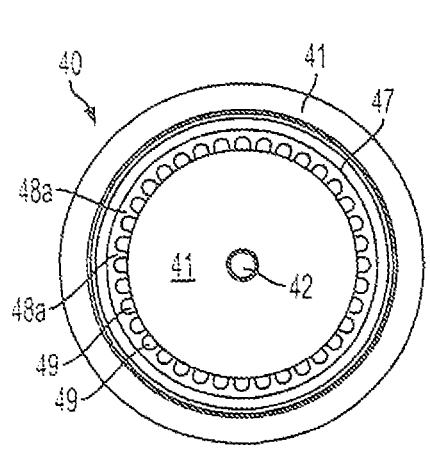
Figure 5:
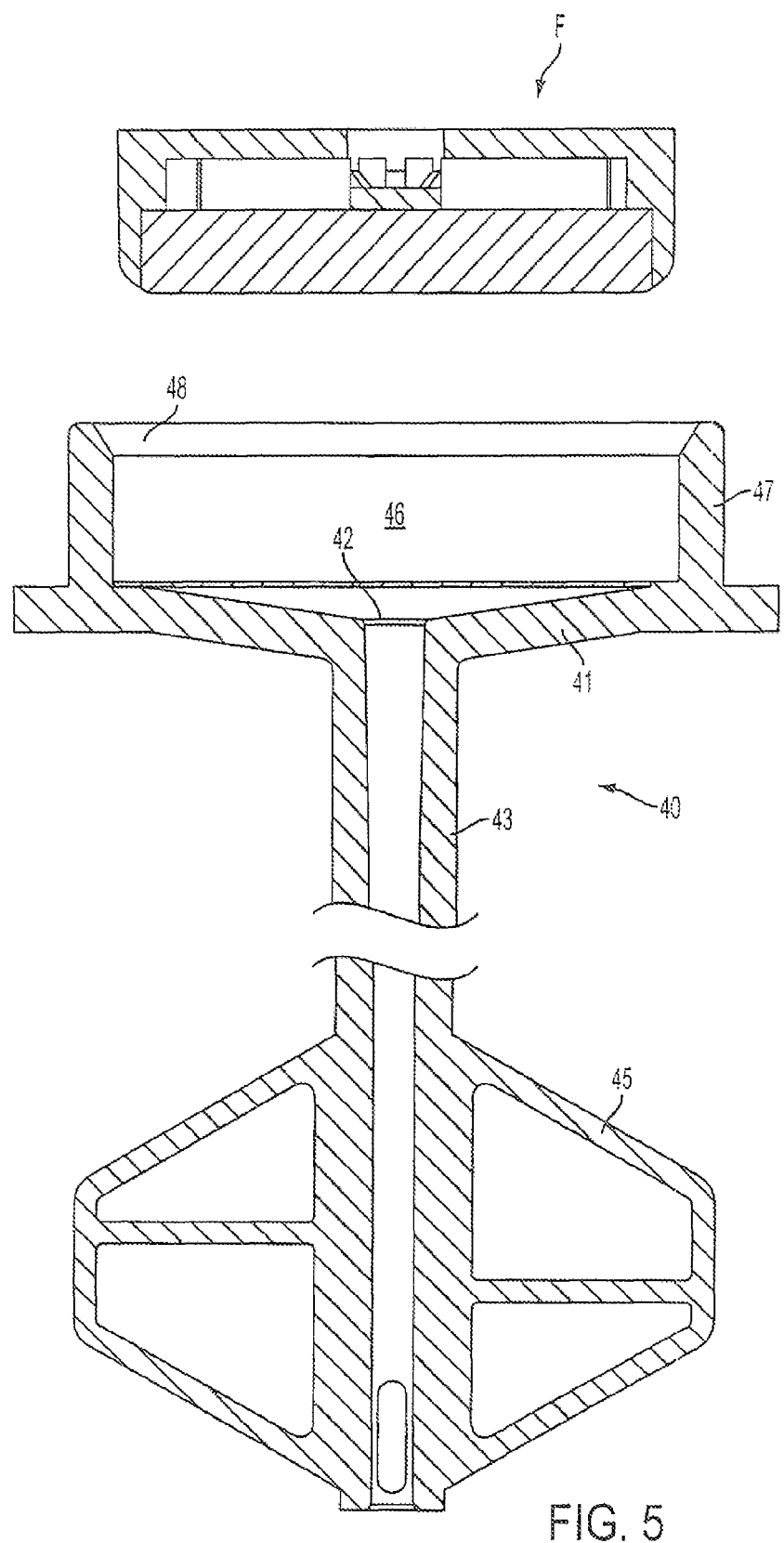

Referring to FIGS. 1, 3 and 5, processing assembly 40 is in the form of a stirrer molded of plastic, preferably polypropylene, having a circular base or bottom wall 41, sloped at its center, with a central inlet port 42; a central depending suction tube 43 with two diametrically opposed suction ports 44 near the bottom of the tube; and a dispersing element in the form of laterally extending vanes 45. The upper portion of the stirrer 40 has a cup-shaped particulate matter separation chamber or manifold 46 defined by base 41 and an upstanding annular wall 47. The upper edges of wall 47 are beveled, the inner edge 48 preferably being beveled to a greater degree to facilitate placement of a filter assembly F in manifold 46, as described below.

Annular wall 47 serves as a coupler for releasably coupling the stirrer 40 to cap liner 32, and is therefore dimensioned to fit snugly within annular coupler 35 (see FIG. 1). Specifically, there is a friction or press fit between couplers 35 and 47 such that normal handling of the closed vial, and normal handling of cover 30 when removed from container 20 (e.g., to place a biological specimen in the container) will not cause separation of the stirrer from the cover. Coupler 47 is dimensioned relative to coupler 35 so that there is a very slight initial diametrical interference, preferably about 0.31 mm. Coupler 47 is stiffer than coupler 35, so assembly of the stirrer to the cover involves slight deformation principally of coupler 35, resulting in a frictional force that keeps the stirrer and the cover engaged. Application of an external force to the vial that overcomes this frictional retention force will cause stirrer 40 to detach from cover 30 and drop by gravity further into container 20 (see FIG. 8).

The external separation force preferably is applied to the central portion of cover 30 (see the arrow in FIG. 8), which deflects cap 31 and liner 32 inwardly. As illustrated in FIG. 1, central boss 36 on liner 32 is dimensioned such that its distal end just contacts or lies very close to base 41 of the stirrer. Thus, when the central portion of the cover is depressed, central boss 36 will deflect further than annular coupler 35 on liner 32 and push stirrer 40 out of engagement with coupler 35. Inward deflection of liner 32 also causes coupler 35 to spread outwardly, thereby lessening the retention force and facilitating detachment of the stirrer. The separation force applied to cover 30 and required to detach the stirrer should be in the range of b 10 to 30 lbs., preferably about 12 lbs.

Another way to detach the stirrer from the cover is to exert an abrupt upward external force on the vial, either manually or mechanically (automatically), to yield an acceleration force that overcomes the frictional retention force and effectively pulls the stirrer out of engagement with the cover. This can be done by, e.g., moving the closed vial rapidly downwardly to rap the bottom of the container 20 against a rather hard surface. Automated vial handling machinery can accomplish this by, e.g., mechanically and/or pneumatically thrusting the closed vial into the carrier that will hold the vial during the subsequent processing steps, or by dropping the vial down a chute into the carrier a sufficient distance to dislodge the stirrer. Another way to exert an abrupt upward external force on the vial is to strike the bottom of the container 20 with a striking member. Automated vial handling machinery can accomplish this by, e.g., cradling the container 20 and momentarily thrusting a striker against the bottom of the container, e.g. through a bottom opening in the vial carrier. The design of these and other variants of suitable automated mechanisms for accomplishing these tasks should be within the grasp of those skilled in the mechanical arts.

Once detached from the cover 30, stirrer 40 comes to rest on the upper ends 27 of ribs 26. See FIG. 8. The particulate matter separation chamber (manifold) 46 thus is stably supported near the container opening and easily accessed by processing equipment, whether manual or automatic, which will manipulate the stirrer so as to process the specimen directly in the container. At least three ribs 26 are required to form a stable support for the stirrer, but four are preferred because that number seems to promote more thorough dispersion of the particulate matter in the liquid during stirring.

FIG. 14 shows an overview and some details of one form of automated (computer-controlled) device for handling specimen vials according to the invention. The device is referred to as an "LBP" device (for liquid-based slide preparation), and can be integrated into a complete automated laboratory system. Further details of the LBP device and the system are set forth in the above-referenced concurrently filed provisional patent application U.S. Ser. No. 60/372,080 entitled "Automated System and Method for Processing Multiple Liquid-Based Specimens."

In the LBP device a conveyor 100 trained around sprockets 102, 104 is driven stepwise in accordance with a specified operating protocol to advance specimen vials along a processing path from one operating head to another. Conveyor 100 has thirty vial carriers 106 (numbered 1-30) serially linked by pins 108. Vial carriers 106 are in the form of receptacles that are keyed to accept containers 20 in only one position (i.e., keyed to notches 25 in containers 20). Loading of vials into conveyor 100 can be done manually, or automatically by a pick-and-place auto loader 110. Unloading of processed containers can be done manually, or by the same or a different pick-and-place auto loader.

Figure 9:
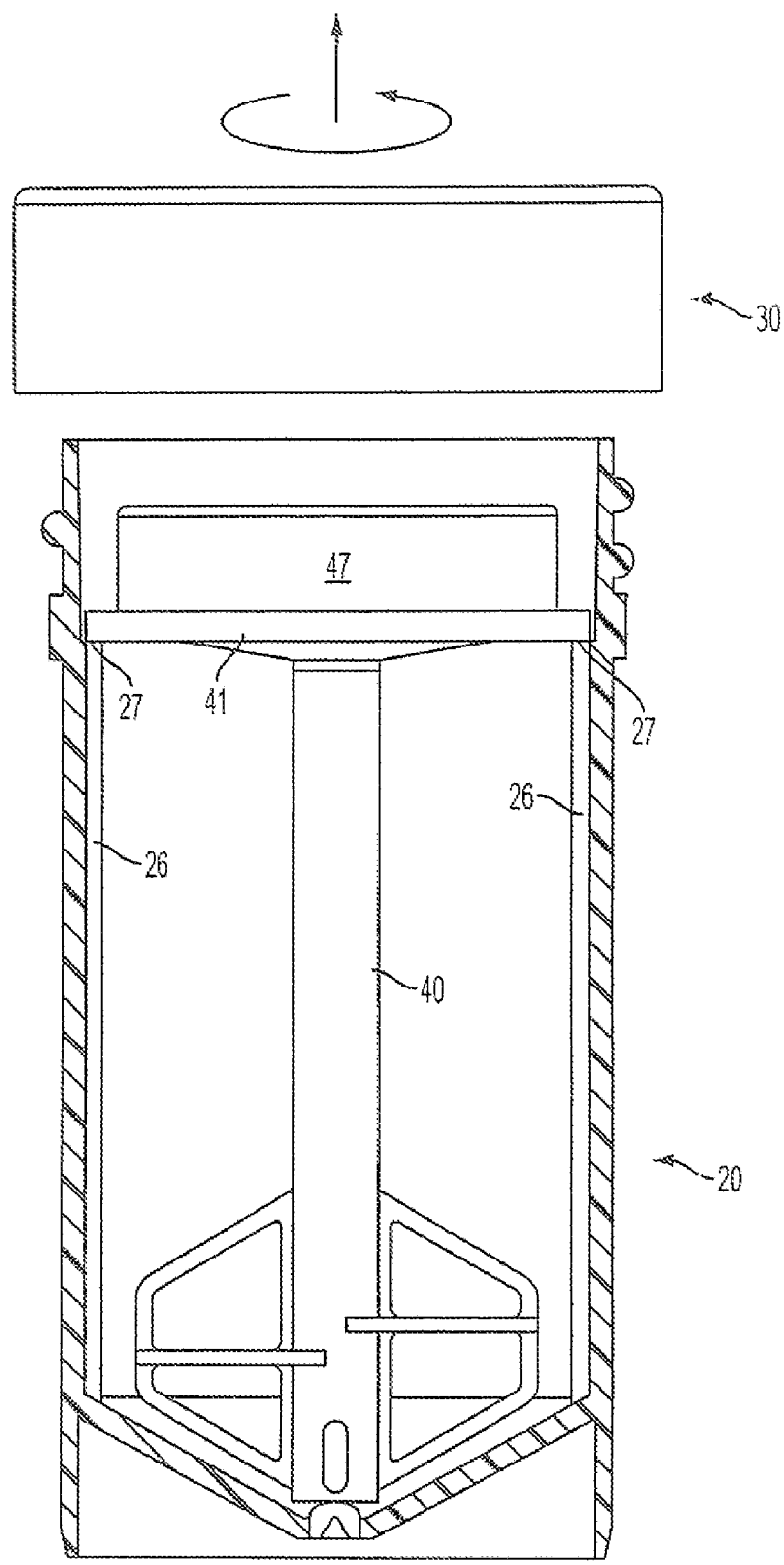
Figure 10:
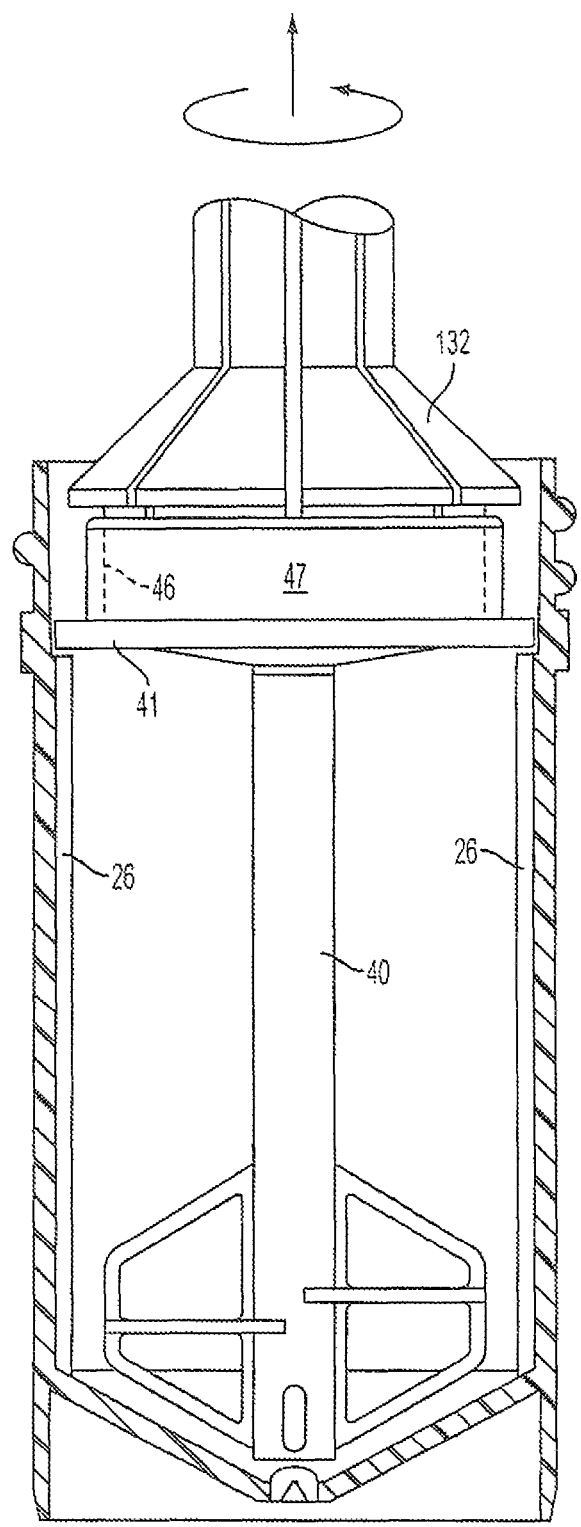
Figure 11:
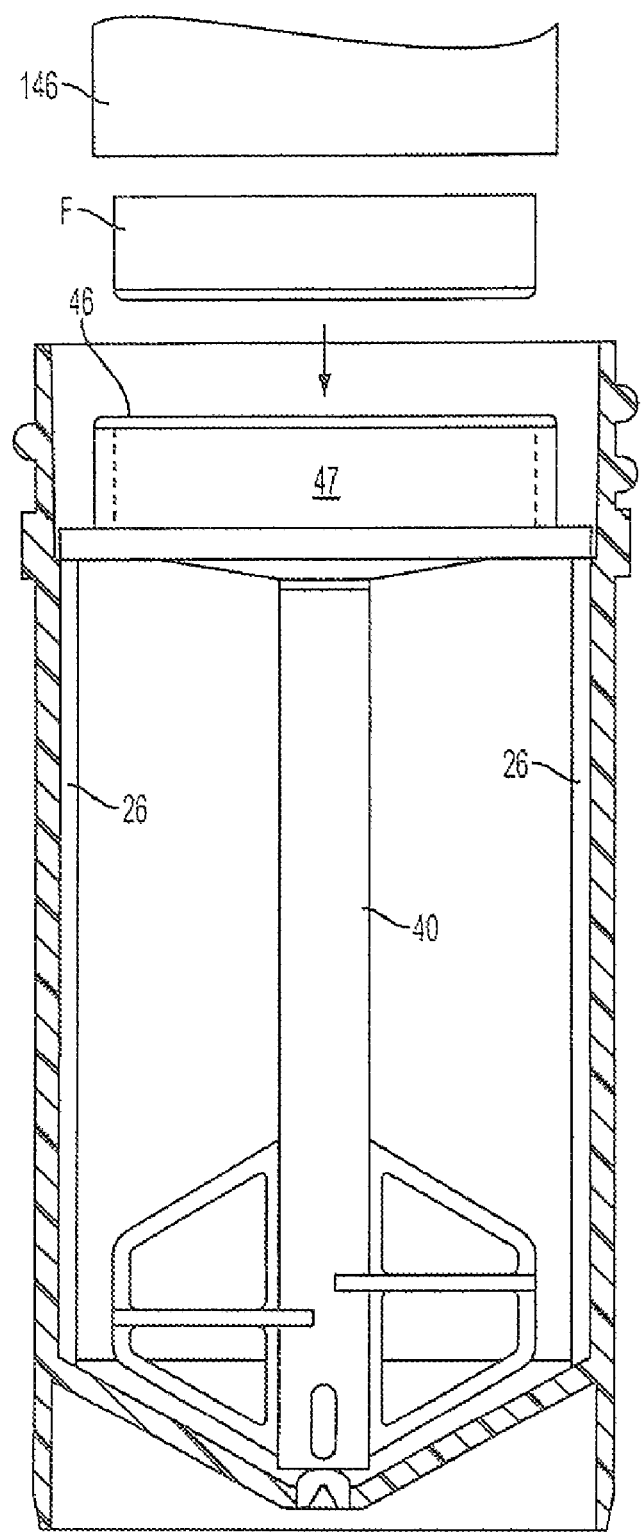
Figure 12:
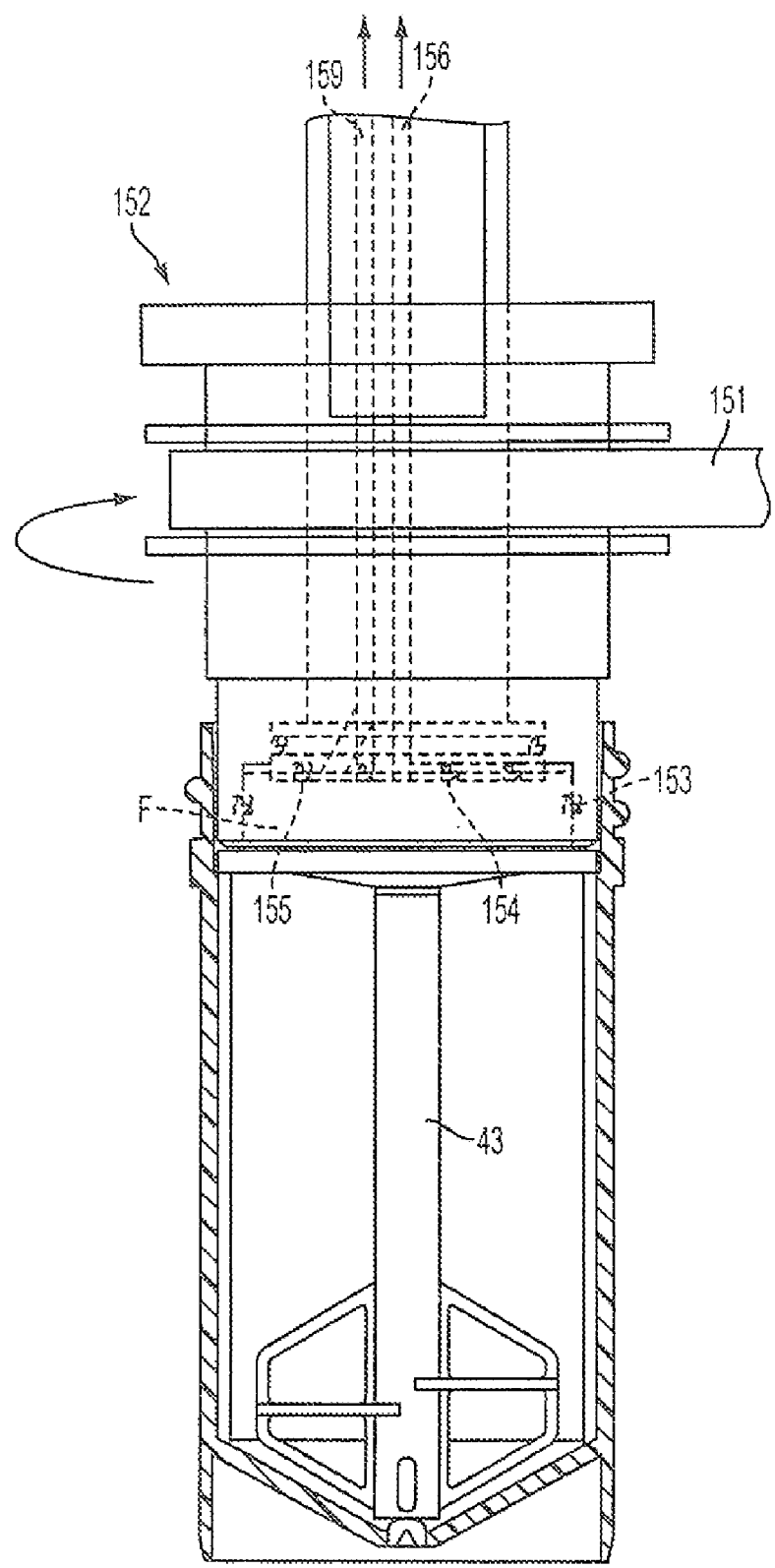

After a specimen vial is loaded into a receptacle 106, data concerning the specimen therein, including the identity of the patient, is first acquired at a bar code reading station 112. This data governs the particular operating protocol to be carried out. The vial then moves to an uncapping station 120, where an uncapping head having a lead screw-driven plunger (not shown) first applies a downward force to the center of the cover (see FIG. 8) to dislodge stirrer 40 from the cover, and then grips the knurled rim of the cover (e.g., using a tapered gripping jaw, not shown), twists it counterclockwise to remove the cover, and then discards it. FIG. 9 schematically illustrates the cover removal step, and shows the stirrer resting on ribs 26 after the cover is removed.

After uncapping the vial moves to a primary stirring station 130 where high-speed stirring is carried out. Here (see FIG. 10) a stirring head comprising an expanding collet 132 moves downwardly by action of a lead screw (not shown) into the open upper recess (manifold) 46 of the stirrer 40, and expands against annular wall 47 to grip the stirrer. The collet lifts the stirrer very slightly so that it clears the ribs 26, and then spins the stirrer in accordance with the sample-specific stirring protocol as determined by the bar code reader 112. The base or bottom wall 41 of the stirrer acts as a slinger to thrust any liquid that may rise along the stirrer against the container wall 21, and prevents the escape of liquid from the container. When stirring is complete, the collet 132 releases the stirrer and rises to clear the container so that it can move on.

At the next station 140 a filter assembly F is loaded into the particulate matter separation chamber (manifold) 46 at the upper end of the stirrer. See FIG. 11. The filter assembly is dispensed by a lead screw-driven pusher 142 from a magazine 144 having eight filter tubes 146 which can house filters of different types. The filter dispensed is determined by the specimen-specific processing protocol.

After a filter assembly F is loaded the vial moves to a specimen acquisition station 150. Here a suction head 152 (see FIG. 12) descends by operation of a lead screw (not shown) to engage the upper portion of the stirrer 40. The suction head has an O-ring 153 that seals against the outside of annular wall 47, and two concentric O-rings 154, 155 that seal against the top of filter assembly F. An inner suction line 156 draws a vacuum on filter F, in accordance with the specimen-specific processing protocol, to aspirate particulate matter-containing liquid from the container through suction tube 43, into the particulate matter separation chamber (manifold) 46 and through the filter assembly F, leaving a monolayer of cells on the bottom surface of the filter as described below. Prior to aspiration the specimen may be stirred again, this time more slowly, to re-suspend the particulate matter in the liquid. This is done by the rotatably mounted suction head 152, which is turned by a timing belt 151.

When aspiration of the specimen is complete, the suction head 152 is raised. The inner portion 158 of the suction head is extended at the same time by action of a pneumatic cylinder (not shown). As the suction head 152 is raised, the outer portion 157 of the suction head disengages from the stirrer 40 (see FIG. 13), but the filter assembly F is retained on the inner portion 158 of the suction head by application of vacuum through suction line 159 to the annular space between O-rings 154 and 155. Thus the suction head 152 removes filter assembly F from the stirrer, and can continue to apply light suction via suction line 156 through the filter to effect a desired degree of moisture control of the cellular material on the filter. The suction head 152 then pivots about an axis 161 (see FIG. 14) to position the filter over a microscope slide S delivered from a slide cassette 162 at a slide presentation station 160. The suction head then moves downwardly to press the filter against the slide S and transfer the monolayer of cells thereto. The phantom lines in FIG. 13 show this change in position of suction head 152 and contact of the filter with slide S. A few drops of liquid fixative are then applied to the specimen on the slide, and the slide is shuttled back to its original position in the slide cassette.

After the specimen has been acquired, the container moves to a recapping station 170 where a new cap, e.g., a heat-sealed foil, is applied to seal the container.

Figure 6:
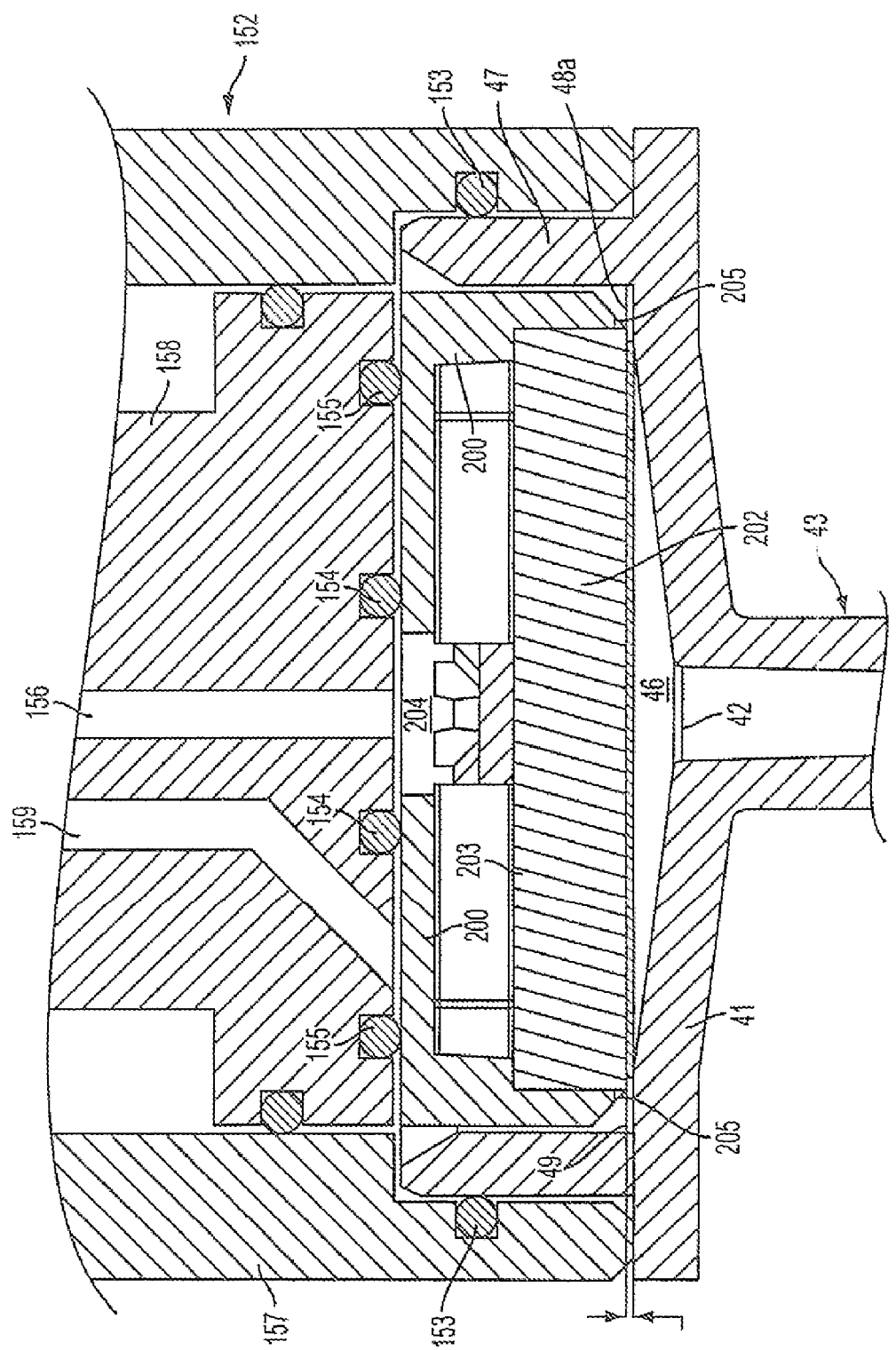
Figure 7:
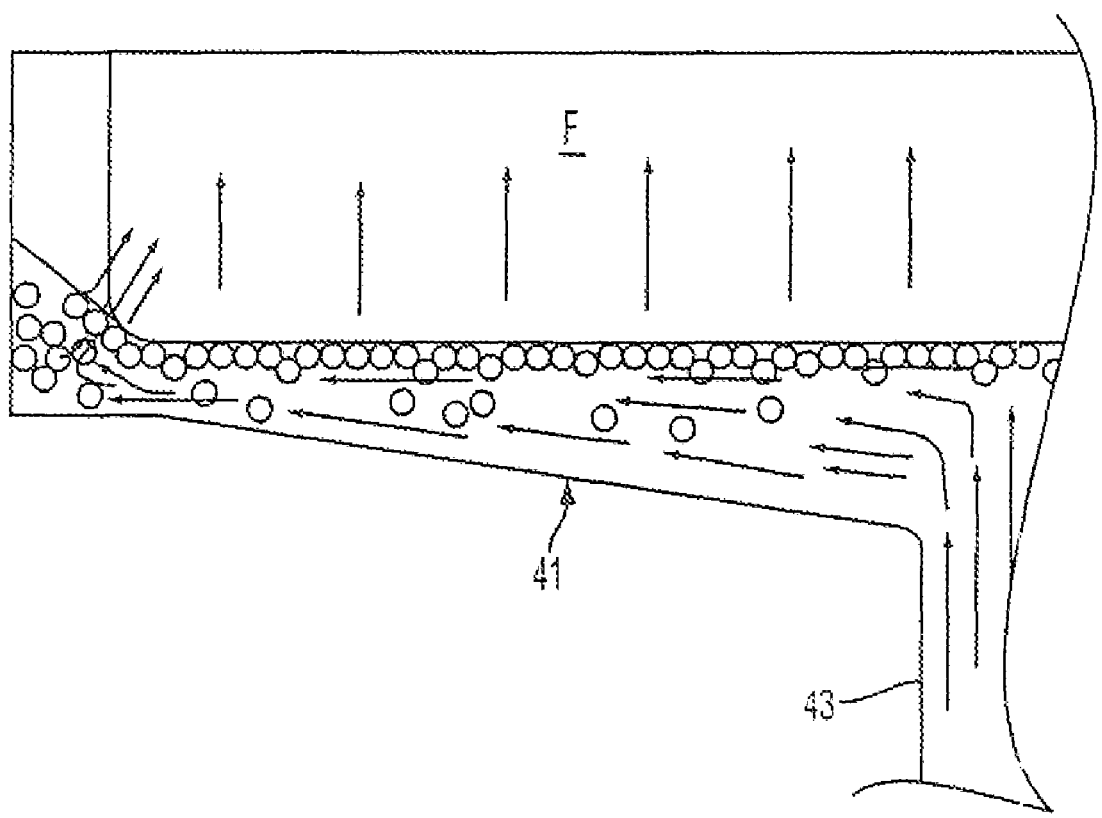

FIG. 6 shows some details of the filter assembly F and its functional cooperation with the stirrer manifold 46 and the inner portion 158 of suction head 152. Filter assembly F comprises a filter holder 200 that accommodates a filter 202. Filter 202 comprises a porous frit 203 and a filter membrane 205 that lies over the lower surface of the frit 203 and is sealed to the periphery of holder 200, e.g., by sonic welding. There is a single, central opening 204 in the top of filter holder 200. The filter 202 (and hence the entire filter assembly F) is supported at its periphery on stirrer base 41 by an array of ribs 48a that define between them radial flow passages 49 (see FIG. 3). The O-rings 154, 155 of inner suction head portion 158 seal against the top of filter holder 200. Suction applied through port 156 creates a vacuum around central opening 204 and within the filter holder 200, which draws liquid into the separation chamber (manifold) 46 and through the filter 202. The flow is vertical through the filter and also across the filter membrane face because of the radial flow passages 49. See FIG. 7, which shows particulate matter (cells) as circles and indicates the flow by arrows. This dual-flow configuration promotes the formation of a monolayer of cells on the filter. See, e.g., the aforementioned U.S. Pat. No. 5,471,994, which describes this dual-flow concept in general. The sloped bottom wall 41 of the manifold 46 further promotes the formation of a monolayer of cells. The constructional details of the filter assembly and its cooperation with the sloped-bottom manifold 46 are set forth in the aforementioned concurrently filed provisional patent application entitled "Automated System and Method for Processing Multiple Liquid-Based Specimens."

The invention thus provides an efficient, inexpensive, convenient and safe vial-based system and method for collecting, handling and processing biological specimens and other specimens of particulate matter-containing liquid. It is ideally suited for use in automated equipment that provides consistently reliable processing tailored to sample-specific needs. Should the stirrer inadvertently become detached from the cover at the point-of-care site, the physician simply places the stirrer loosely in the vial so that it descends into the specimen and then screws the cover on as usual. This is not difficult because the ribs in the vial allow insertion of the stirrer in only one direction. Once the vial is closed with the specimen inside, the stirrer remains in the vial throughout processing and is sealed therein when the vial is re-capped.

Various modifications will be apparent to those skilled in the art without departing from the scope of the invention, which is defined by the appended claims.

What is claimed is:

1. A method for processing particulate matter-containing liquid held in a vial,
    the vial comprising:
        a container having an opening at an upper end thereof;
        an imperforate cover removably coupled to the container to close the opening; and
        a processing assembly that is separate from the container and is coupled to the cover proximate an interface between the cover and the opening by a releasable coupling that allows the processing assembly to be removed from the container along with the cover while still coupled thereto, the releasable coupling comprising mating couplers in the form of closely fitting projections held together by a frictional retention force and respectively carried by the inside of the cover and an upper portion of the processing assembly such that the couplers disengage upon application of an external force to the vial that overcomes the retention force, whereby the processing assembly may be selectively detached inwardly from the cover while the cover is on the container so that the processing assembly remains in the container when the cover is subsequently removed;
    the method comprising:
        detaching the processing assembly from the cover while the cover is on the container;
        removing the cover to expose the detached processing assembly in the container; and
        manipulating the processing assembly so as to process the particulate matter-containing liquid in the container.

2. The method of claim 1, wherein detaching the processing assembly comprises applying an external force to the closed vial.

3. The method of claim 2, wherein detaching the processing assembly comprises applying the external force to the central portion of the cover to deflect the cover inwardly.

4. The method of claim 1, the processing assembly comprising a dispersing element, wherein manipulating the processing assembly comprises moving the dispersing element to thereby disperse the particulate matter in the liquid.

5. The method of claim 4, wherein moving the dispersing element comprises rotating the processing assembly to cause the dispersing element to stir the particulate matter-containing liquid.

6. The method of claim 4, wherein moving the dispersing element comprises lifting the processing assembly slightly to insure clearance between the processing assembly and the container, and thereafter rotating the processing assembly to cause the dispersing element to stir the particulate matter-containing liquid.

7. The method of claim 5, wherein the processing assembly further comprises (i) a particulate matter separation chamber at the upper portion thereof adapted to hold a filter assembly, and (ii) a tube communicating with the separation chamber and extending downwardly therefrom, and wherein manipulating the processing assembly further comprises placing a filter assembly in the separation chamber, sealing the separation chamber, and applying a vacuum to the separation chamber to draw the stirred particulate matter-containing liquid upwardly through the tube and into contact with the filter assembly so as to collect particulate matter on a surface of the filter assembly.

8. The method of claim 7, further comprising removing the filter assembly from the separation chamber, and contacting the particulate matter collected on the filter assembly with a slide so as to transfer collected particulate matter to the slide.

9. A method for processing particulate matter-containing liquid held in a vial,
    the vial comprising:
        a container having an opening at its upper end, a central axis extending lengthwise of the container through the opening, and a wall surrounding the axis;
        a cover removably coupled to the container to close the opening; and
        a processing assembly separate from and wholly within the container and engageable by an external manipulator after the cover is removed, wherein a portion of the surrounding container wall below the opening loosely supports the processing assembly when it is not engaged by a manipulator such that an upper portion of the processing assembly is disposed near but not above the opening, the supporting portion of the container wall comprises at least three spaced inwardly extending supports on which the processing assembly rests, wherein the processing assembly comprises a particulate matter separation chamber at the upper portion thereof adapted to hold a filter assembly, a tube communicating with the separation chamber and extending downwardly therefrom, and a dispersing element carried by the tube, the upper portion of the processing assembly having a peripheral portion that lies close to the surrounding wall and rests on the supporting portion of the surrounding wall;
    the method comprising:
        detaching the processing assembly from the cover while the cover is on the container;
        removing the cover to expose the detached processing assembly in the container; and
        manipulating the processing assembly so as to process the particulate matter-containing liquid in the container.

10. The method of claim 9, wherein detaching the processing assembly comprises applying an external force to the closed vial.

11. The method of claim 10, wherein detaching the processing assembly comprises applying the external force to the central portion of the cover to deflect the cover inwardly.

12. The method of claim 9, wherein manipulating the processing assembly comprises moving the dispersing element to thereby disperse the particulate matter in the liquid.

13. The method of claim 12, wherein moving the dispersing element comprises rotating the processing assembly to cause the dispersing element to stir the particulate matter-containing liquid.

14. The method of claim 12, wherein moving the dispersing element comprises lifting the processing assembly slightly to insure clearance between the processing assembly and the container, and thereafter rotating the processing assembly to cause the dispersing element to stir the particulate matter-containing liquid.

15. The method of claim 14, wherein manipulating the processing assembly further comprises placing a filter assembly in the separation chamber, sealing the separation chamber, and applying a vacuum to the separation chamber to draw the stirred particulate matter-containing liquid upwardly through the tube and into contact with the filter assembly so as to collect particulate matter on a surface of the filter assembly.

16. The method of claim 15, further comprising removing the filter assembly from the separation chamber, and contacting the particulate matter collected on the filter assembly with a slide so as to transfer collected particulate matter to the slide.

17. A method for processing particulate matter-containing liquid held in a vial, the vial comprising:
a container having an opening at its upper end, a central axis extending lengthwise of the container through the opening, and a wall surrounding the axis;

a cover removably coupled to the container to close the opening; and a processing assembly separate from and wholly within the container and engageable by an external manipulator after the cover is removed, wherein a portion of the surrounding container wall below the opening loosely supports the processing assembly when it is not engaged by a manipulator such that an upper portion of the processing assembly is disposed near but not above the opening, the processing assembly comprising a particulate matter separation chamber at the upper portion thereof adapted to hold a filter assembly, a tube communicating with the separation chamber and extending downwardly therefrom, and a dispersing element carried by the tube, the upper portion of the processing assembly having a peripheral portion that lies close to the surrounding wall and rests on the supporting portion of the surrounding wall, the processing assembly rotatable about the central axis so as to cause the dispersing element to stir the particulate matter-containing liquid and dimensioned to rotate freely in the container without contacting the surrounding wall when lifted slightly off the supporting portion of the surrounding wall by a rotating manipulator, wherein the supporting portion of the container wall comprises at least three spaced inwardly extending supports on which the peripheral portion of the processing assembly rests;

the method comprising:
detaching the processing assembly from the cover while the cover is on the container;

removing the cover to expose the detached processing assembly in the container; and manipulating the processing assembly so as to process the particulate matter-containing liquid in the container.

18. The method of claim 17, wherein detaching the processing assembly comprises applying an external force to the closed vial.

19. The method of claim 18, wherein detaching the processing assembly comprises applying the external force to the central portion of the cover to deflect the cover inwardly.

20. The method of claim 17, wherein manipulating the processing assembly comprises moving the dispersing element to thereby disperse the particulate matter in the liquid.

21. The method of claim 20, wherein moving the dispersing element comprises rotating the processing assembly to cause the dispersing element to stir the particulate matter-containing liquid.

22. The method of claim 20, wherein moving the dispersing element comprises lifting the processing assembly slightly to insure clearance between the processing assembly and the container, and thereafter rotating the processing assembly to cause the dispersing element to stir the particulate matter-containing liquid.

23. The method of claim 22, wherein manipulating the processing assembly further comprises placing a filter assembly in the separation chamber, sealing the separation chamber, and applying a vacuum to the separation chamber to draw the stirred particulate matter-containing liquid upwardly through the tube and into contact with the filter assembly so as to collect particulate matter on a surface of the filter assembly.

24. The method of claim 23, further comprising removing the filter assembly from the separation chamber, and contacting the particulate matter collected on the filter assembly with a slide so as to transfer collected particulate matter to the slide.

* * * * *